US006280776B1

(12) United States Patent
Sha et al.

(10) Patent No.: US 6,280,776 B1
(45) Date of Patent: Aug. 28, 2001

(54) **COMPOSITION COMPRISING *PANAX PSEUDO GINSENG* AND *EUCOMMIAE ULMOIDES***

(75) Inventors: Shinhan Sha, 7-11, Nishiikebukuro-2-chome, Toshima-ku, Tokyo; Noboru Yanaihara, Shizuoka, both of (JP)

(73) Assignee: Shinhan Sha, Tokyo (JP)

( * ) Notice: Subject to any disclaimer, the term of this patent is extended or adjusted under 35 U.S.C. 154(b) by 0 days.

(21) Appl. No.: 09/382,596

(22) Filed: Aug. 25, 1999

(30) Foreign Application Priority Data

Nov. 13, 1998 (JP) .................................. 10-323941

(51) Int. Cl.$^7$ .................................. A61K 35/78
(52) U.S. Cl. .................. 424/728; 424/757; 424/773
(58) Field of Search ................ 424/195.1, 728, 424/773, 757

(56) References Cited

U.S. PATENT DOCUMENTS

| 4,446,130 | * | 5/1984 | Hachiya et al. | .................. 424/195.1 |
| 5,589,182 | * | 12/1996 | Tashiro et al. | .................... 424/195.1 |
| 6,123,946 | * | 9/2000 | Wei | .................................. 424/195.1 |

FOREIGN PATENT DOCUMENTS

| 1084754 | * | 4/1996 | (CN) . |
| 8-073369 |   | 3/1996 | (JP) . |
| 9-023851 |   | 1/1997 | (JP) . |

OTHER PUBLICATIONS

Computer JPAB Abstract JP408191668 Kanamaru "Pet Food" Jul. 30, 1996.*
Computer Derwent Abstract 1997–539684 Taisho Parm Co. Ltd JP 09227394 "Oral Composition with Tranquilliser Effect—Contains Rhizomes of *Eleuterococcus senticocus*, Bark of *Eucommiae ulmoides* Oliv." Sep. 2, 1997, Jul. 1997.*

Computer Toxline Abstract 1995:105742 Kosuge et al J. Pharm. Soc. Jap (1981) vol. 101 No. 6 pp 501–503.*

Computer Napralert Abstract 94:3763 Yang Zhejiang–Zhongyi Zazhi (1989) 24 (9) 397–398, Jul. 1996.*

Matsushima, "Rinsho & Kenkyu", vol. 56(10), 345(3461) (1979).

Y. Ishii, Japan J. Pharmaco., 120 71 (1971).

"Preventive effects of the extract of Du–Zhong (Tochu) leaf and Ginseng root on acute toxicity of chlorpyrifos," Japanese Journal of Toxicology and Environmental Health 1997, vol. 43, No. 2, pp. 92–100 (abstract).

"Mechanism of the protective effects of sumac gall extract and gallic acid on the progression of CC14–induced acute liver injury in rats," American Journal of Chinese Medicine 1998, vol. 26, No. 3–4, pp. 333–341 (abstract).

Computer Derwent Abstract JP09023851 Jan. 28, 1997.*

Computer Derwent Abstract 1995–194715 Inventor He, T; CN1084754 Apr. 6, 1994.*

* cited by examiner

*Primary Examiner*—Herbert J. Lilling
(74) *Attorney, Agent, or Firm*—Finnegan, Henderson, Farabow, Garrett & Dunner, L.L.P.

(57) ABSTRACT

A composition comprising "*Panax Pseudo Ginseng*" and "*Eucommia Bark*", a composition comprising gallic acid-containing herbal extracts and "*Licorice Root*", together with "*Panax Pseudo Ginseng*" and "*Eucommia Bark*", a drink or food comprising the above composition, and medicines, food supplements, healthcare foods, mixing feed and feed for improvement of nutritional state, hypertension, high blood sugar, immune system and liver disorders.

23 Claims, No Drawings

COMPOSITION COMPRISING *PANAX PSEUDO GINSENG* AND *EUCOMMIAE ULMOIDES*

BACKGROUND OF THE INVENTION

1. Field of the Invention

The present invention relates to compositions comprising "*Panax pseudo-ginseng*" and "*Eucommiae ulmoides (Eucommia Bark)*", and, if desired, comprising gallic acid-containing herbal extracts and "Licorice Root" additionally and provides a method for its production.

The composition of the present invention can be used effectively not only for human healthcare and improvement of nutritional state and immune system, but also for therapeutics or protection against hepatitis and infectious diseases, as conventional or alternative medicine and food supplements.

In addition, the composition of the present invention can be used as food supplements not only for protection against hypertension and diabetes mellitus of animals such as dogs, cats, pigs, cattle, horses and others, but also for healthcare and improvement of the nutritional state and immune system of these animals including birds and fish.

2. Description of the Related Art

Results of a nationwide survey indicate a marked increase in the number of individuals, who suffered from overweight, hypertension and diabetes mellitus, because of their environmental conditions, lack of exercise and high-calorie diets. Accordingly, ability for protection against hepatitis, infectious disease and immune disease will be markedly lowered.

These observations can be seen in the animal's environment. In fact, pet animals kept in a small area, e.g., in the rooms of a house, tend to suffer from disorders of nutritional state, hypertension, psychosomatic stress and overweight bodies with high fat mass.

On the other hand, increase of a patient's suffering with HBV and HCV are also serious problems to be solved.

In general, interferons have been used for therapy of patients suffering with HBV and HCV, although interferons had been known to have strong unfavorable side effects.

SUMMARY OF THE INVENTION

It is an object of this invention to provide food supplements and alternative medicines having an effect for significant improvements in symptoms such as high cholesterol, hypertension, diabetes mellitus and some cancers (in order to keep in healthy condition).

A further object is to provide alternative medicines which afford significant improvements in the symptoms of HBV and HCV, when compared with therapy with interferons.

The first objects of this invention have been attained by providing food supplements and the related products and alternative medicines comprising "Panax pseudo-ginseng" and "Eucommiae ulmoides", and if desired, comprising gallic acid-containing herbal extracts and "Licorice root (Glycyrrhiza glabra)".

Still another object of this invention is to provide alternative medicine comprising "*Panax pseudo-ginseng*", "*Eucommiae ulmoides*", and if desired, comprising gallic acid-containing herbal extracts and "Licorice Root", which are effective for therapy in symptoms with various liver disorders.

Also provided herein are compositions comprising "*Panax pseudo-ginseng*", "*Eucommiae ulmoides*", gallic acid-containing herbal extracts and Licorice root (*Glycyrrhiza glabra*), which are useful as food supplements for healthcare, alternative medicine for therapy of liver disorders, supplemental products, products for drink, animal foods and food compounds for animals, birds and fish.

The present invention provides a method for production of the above-mentioned composition which comprises obtaining condensed extracts of "*Panax pseudo-ginseng*" and "*Eucommiae ulmoides*" by condensing hot-water extracts of minced dry "*Panax pseudo-ginseng*" and "*Eucommiae ulmoides*", and if desired, their pulverized product by heat drying; obtaining condensed extracts of gallic acid-containing herbal extracts by condensing hot-water extracts of minced dry gallic acid-containing herbal extracts and if desired their pulverized products by heat drying; and mixing and then drying extracts or pulverized products of "*Panax pseudo-ginseng*" and "*Eucommiae ulmoides*", extracts or pulverized products of gallic acid-containing herbal extracts, and extracts or pulverized products of "Licorice Root".

Alternative medicines, food supplements, products for drinking and healthcare food for humans and animals comprising the above compositions are effective for lowering blood, sugar and cholesterol and for enhancing the immune system.

In addition, the composition of the present invention shows the effect of lowering the elevated GOT and GTP levels. Especially, oral administration of compositions containing gallic acid-containing herbal extracts resulted in the reduction of elevated a-Fetoprotein and albumin in humans, suggesting that compositions of the present invention may be effective for prevention or reduction of the symptoms connected with high blood cholesterol, hypertension and diabetes mellitus, and also useful for prevention of chronic hepatitis. Although gallic acid-containing herbal extracts themselves have been known to be difficult to absorb into human or animal bodies, compositions of this invention comprising gallic acid-containing herbal extracts can be readily absorbed into human and animal bodies.

DESCRIPTION OF THE PREFERRED EMBODIMENTS

This invention utilizes the root of *Panax pseudo-ginseng* (Wall). This Chinese herb has been known to improve lipid metabolic failure, and to control hypertension and pain relief.

Eucommia bark generally consists of dried bark of Eucommiae ulmoides. This Chinese herb has been known to reduce hypertension and high blood lipid level.

The Eucommiae ulmoides in this invention, however, not only refers to "Eucommia bark" but also includes leaves and fruits of Eucommiae ulmoides.

"Denhichi-Tochu-Sei" is a novel composition of Chinese herbs comprising Panax pseudo-ginseng and Eucommia bark, which was invented by the present inventors. "Denhichi-Tochusei" is produced by extracting the root of Panax pseudo-ginseng and the Eucommiae ulmoides with hot water. The composition "Denhichi-Tochu-Sei" can contain honey and Panax ginseng (Chinese Ginseng) as additives.

The word "Denhichi-Tochu-Sei" of the present invention indicates the composition comprising dried extracts of Chinese herbs, such as Panax Pseudo Ginseng and Eucommia mainly.

In "Denhichi-Tochu-Sei" of the present invention the compositions of Chinese herbs are Panax pseudo-ginseng (Denhichi) 10~90 weight %, Eucommiae ulmoides (Tochu) 10~90 weight %, Panax ginseng (Chinese Ginseng), 0~20 weight %, preferably 5~20 weight %, and honey 0~30 weight %. A preferable composition for Denhichi-Tochu-Sei of the present invention is 30 weight % of Panax pseudo-ginseng, 40 weight % of Eucommiae ulmoides, 20 weight % of Panax ginseng (Chinese Ginseng) and 10 weight % of honey, or 30 weight % of Panax pseudo-ginseng, 40 weight % of Eucommiae ulmoides, 10 weight % of Panax ginseng (Chinese Ginseng), 10 weight % of honey and 10 weight % of others.

In this invention, although the most preferable ratio of Panax pseudo ginseng and Eucommiae ulmoides in the composition is 3:4, even at the 1:0.1~1:9 ratio, biological effects such as lowering blood pressure and blood cholesterol and enhancing immune condition are still retained.

Gallic acid is 3,4,5-trihydroxybenzoic acid, which is contained in "Gallae halepensis", "Gallae rhois", "Gallae chinensis" as well as other herbs, which are used as Chinese medicines. The gallic acid-containing herbal extracts include these Chinese medicines.

Licorice root was obtained from the roots or kernels of Glycyrrhiza glabra Linn.

Glycyrricine, which is a main component of Licorice root, has been known to improve several symptoms with liver injuries and to elevate the serum transaminase by the double blind examination.

Further, glycyrricine has been shown to protect $CCl_4$-induced liver injury (Matsushima, Rinsho & Kenkyu, vol. 56(10), 345–(3461)(1979)).

Composition (Denhichi-Tochu-Sei) and compositions containing Denhichi-Tochu-Sei, extracts of Gallae rhois and Licorice root in the present invention, dissolve in water and are readily absorbed into the living body, and were found to afford the effects continuously.

Especially, granules or tablets obtained by drying under heating the composition comprising Gallae rhois, Licorice root, "Denhichi-Tochu-Sei" and an emulsifier shows not only the effects of Gallae rhois Licorice root, but also the synergistic effect of "Denhichi-Tochu-Sei", improving the blood cholesterol levels, blood sugar and liver functions.

The composition of this invention can further contain "Siberian Solomonseal Rhizome."

Next, methods for the preparation of the composition of this invention are described.

First, dried Eucommia (leaves, fruit, bark) and dried Panax pseudo ginseng were minced, and the minced mixture was extracted with hot water at 80° C.~120° C. for 0.5~2 hr (extraction step). Then, through filtration and concentration steps, the extracts thus obtained were mixed with Chinese Ginseng (Panax ginseng) and honey (mixing step). Further, by processing under hot air, powdered "Denhichi-Tochu-Sei" is obtained.

In the same manner, gallic acid-containing herbal extracts were obtained by extracting a gallic acid-containing Chinese herb with hot water minced dry Schisandrae, and then concentrating the solution. The powder of gallic acid-containing herbal extracts is obtained by heat drying the extracts.

Emulsifier was added to the above mixture to prepare tablets under heat drying.

Gallic acid-containing herbal extracts and licorice extract can be contained with the above mentioned "Denhichi-Tochu-Sei".

Addition of emulsifier to the mixture produced tablets. By processing the composition as mentioned above, powder, tablet, liquid and food supplements are prepared. Honey, vegetable oil, xylitol or the like can be used as emulsifier. The weight % of the emulsifier is preferably 0~20%.

The mixing ratio of "Denhichi-Tochu-Sei", gallic acid-containing herbal extracts and Licorice root is in a range of 10~80%, 4~20% and 4~15% (weight %), respectively. In the case of gallic acid-containing herbal extracts, a preferable mixing range is 6~12 weight %. In the case of Licorice, a preferable mixing range is 6~11 weight % or 0%, depending on conditions of individual patients.

Especially compositions obtained by mixing powdered panax pseudo-ginseng 60 weight %, "Denhichi-Tochu-Sei" 20 weight %, gallic acid-containing herbal extracts 8 weight %, Licorice 8 weight % and emulsion 4 weight % are favorable for production of various kinds of food supplements.

Compositions of the present invention can be processed as powder, granules, tablets and dry syrup suitable for alternative medicine, food supplements and the like. Content of composition of the present invention is in the range of 0.1~0.5 g per tablet, or in the range of 0.1~30 weight %, preferably 1~5 weight % based on alternative medicine or food supplements.

In the case of tablets obtained by heat drying the mixture of "Denhichi powder", "Denhichi-Tochu-Sei", gallic acid-containing herbal extracts and Licorice, the content of composition of this invention should be 0.25 g/tablet or less.

The proper amount of the aforementioned "Denhichi-Tochu-Sei" for ingestion per day is 0.1~2 g/kg, preferably 0.1~0.25 g/kg.

In the present invention, pet includes animal, bird and fish (dog, cat, monkey, rabbit, chicken, duck, gold fish) which can be raised by human beings.

In addition, pig, cattle and horse (includes racing horse) are included for use.

In addition, the composition of this invention can be added to cakes, candy, bread, wine, liquor, curry and any health-care food.

Detailed explanations of this invention with examples will be made below. Rats (Wister, male) and mice (male) were used in the experiments.

EXAMPLE 1

Analysis of "Denhichi-Tochu-Sei" (granule):

Table 1 shows the analytical data of "Denhichi-Tochu-Sei" (granule), which consists of Panax pseudo-ginseng 30 weight %, Eucommia Bark 40 weight %, ginseng 20 weight % and honey 10 weight %.

In the following Examples, the composition of this Example 1 was used as "Denhichi-Tochu-Sei" (granule).

TABLE 1

Analysis Table of "Denhichi-Tochu-Sei" (granule)

| | |
|---|---|
| Protein content | 8.28% (w/w) |
| Sugar content | 25.30% (w/w) |
| Elementary analysis value | C: 40.95% |
| | H: 6.68% |
| | N: 0.29% |
| Free amino acid: mg/100 g granule | Asp: 2.18 |
| | Ser: 2.74 |
| | Gly: 0.34 |
| | Ala: 0.28 |
| | Gln: 6.41 |
| | Ile: 0.65 |
| | Lys: 1.79 |

Table 2 shows the trace element contents of the above-mentioned "Denhichi-Tochu-Sei" (granule) determined by atomic absorption spectroscopy.

Rats (weight 180~200 g) and mice (weight 18~20 g) were divided into four groups (10 rats and mice for each group). The four groups were A) normal group, B) group with hyperlipemia (prepared by high fat administration), C) group with hyperlipemia (with high dosage of "Denhichi-Tochu-Sei" (granule), and D) group with hyperlipemia (with a low dosage of "Denhichi-Tochu-Sei" (granule). In the C and D groups, "Denhichi-Tochu-Sei" and high fat feed were administered in the stomach through cannula constantly for 30 days. One hour after the last administration, a blood sample was taken from rat ophthalmic vein, from which serum was separated. The serum was examined for the levels of cholesterol, triglyceride, lipoprotein of low molecular weight, LDL and lipoprotein of high molecular weight using Beckman's serum biochemical analyzer CX5. The results are shown in Table 3.

Table 3 clearly shows that addition of "Denhichi-Tochu-Sei" (granule) to the high fat feed prevents the appearance of hyperlipemia. Namely, blood serum cholesterol and lipoprotein of lower molecular weight were reduced and the slight elevation of lipoprotein with higher molecular weight and reduction of triglyceride were observed in group C and group D. In fact, statistical and significant differences were obtained between the values obtained with normal group (A) or group (B) given only high fat feed and the values obtained with groups given a high dosage of "Denhichi-Tochu-Sei" (referring to Table 3).

TABLE 3

The effect of "Denhichi-Tochu-Sei" (granule) on blood serum lipid levels

| Group | Number of Animals | Dosage (g/kg) | Cholesterol (mol/l) | Lipoprotein with higher molecular weight (mol) | LDL (mol/l) | Triglyceride (mol/l) | Lipoprotein with lower molecular weight (mol/l) |
|---|---|---|---|---|---|---|---|
| Normal (control) | 10 | | 1.51 ± 0.2* | 1.06 ± 0.16* | 0.192 ± 0.14* | 0.996 ± 0.43* | 0.52 ± 0.19* |
| Group given high fat feed | 10 | | 15.42 ± 3.5 | 0.34 ± 0.01 | 16.07 ± 1.18 | 2.575 ± 0.92 | 1.09 ± 0.42 |
| Group given high fat feed and high dosage of "Denhichi-Tochu-Sei" extracts | 10 | 2 | 8.91 ± 2.1* | 0.52 ± 0.18* | 7.59 ± 3.14* | 1.89 ± 0.71* | 0.87 ± 0.31* |
| Group given high fat feed and low dosage of "Denhichi-Tochu-Sei" extracts | 10 | 1 | 10.85 ± 1.9* | 0.50 ± 0.13* | 9.45 ± 3.42* | 2.41 ± 0.87* | 0.98 ± 0.24* |

*$P < 0.05$ compared with group given high fat feed

TABLE 2

The results of trace element test of the above-mentioned "Denhichi-Tochu-Sei" (granule)

| Element | μg/g | Element | μg/g |
|---|---|---|---|
| Na | 25.0 | Fe | 7.63 |
| K | 51.0 | Ca | 304 |
| Si | 0.181 | Water | 8.88% |
| Sn | <0.413 | Ash content | 0.42% |
| Mg | 526 | | |
| Zn | 4.39 | | |

EXAMPLE 2

Effect of "Denhichi-Tochu-Sei" (granule) on the Blood Serum Cholesterol of Rats with Hyperlipemia:

EXAMPLE 3

Effect of "Denhichi-Tochu-Sei" (granule) on Mice with Deteriorating Immune System:

Mice were divided into three groups, i.e., a normal group for comparison, a group with deteriorating immune system and a group with deteriorating immune system given "Denhichi-Tochu-Sei" (granule). A comparison of the immune system of these three groups was made. As can be seen in Table 4, the immune system of the individual mouse seems to improve after administrating "Denhichi-Tochu-Sei" (granule).

TABLE 4

Effect of "Denhichi-Tochu-Sei" (granule) on immune system

| Group | Number of Animals | Dosage (g/kg) | K value |
|---|---|---|---|
| Normal group (control) | 10 | | 0.079 ± 0.098 |
| Model group with deteriorating immune system | 10 | | 0.034 ± 0.015 |
| Model group with deteriorating immune system and administration of "Denhichi-Tochu-Sei" (granule) | 10 | 2 | 0.060 ± 0.024 |

*$P < 0.01$ Compared with model group with deteriorating immune system

EXAMPLE 4
Fatigue Durability Test:

Mice (weight 18~20 g) were divided into two groups. One is a normal group, the other is a group given "Denhichi-Tochu-Sei" (granule) throughout for 20 days. The results of a fatigue durability test, which was conducted one hour after the last administration, are shown in Table 5. In the test, a mouse carried an iron with a weight corresponding to 10% of its body weight, attached to its tail and was made to swim in a thermostatic pool of 40 cm length×28 cm width×30 cm depth at a water temperature of 20° C. The time of swimming (sec) was measured. The results are shown in Table 5.

TABLE 5

Swimming time of weighed mice given "Denhichi-Tochu-Sei" (granule)

| Group | Number of Animals | Dosage (g/kg) | Swimming time (sec) |
|---|---|---|---|
| Normal group | 10 | | 60.42 ± 18.81 |
| Group with administration of "Denhichi-Tochu-Sei" (granule) | 10 | 2 | 100.72 ± 31.91 |

*$P < 0.01$

Table 5 clearly shows that the swimming time of the group with administration of "Denhichi-Tochu-Sei" (granule) was significantly longer than the normal group. The results suggest that "Denhichi-Tochu-Sei" (granule) may contribute to the durability for fatigue.

EXAMPLE 5
Effect for Mice with High Blood Sugar:

Mice with blood sugar level of above 180 mg/dl were used in this test. The mice (weight 21~23 g) were divided into three groups, a normal mouse group, a group of mice with high blood sugar level and a group of mice with high blood sugar level, and administered "Denhichi-Tochu-Sei" (granule). They were examined for their blood sugar levels. The results are shown in Table 5. After the mice with high blood sugar level received "Denhichi-Tochu-Sei" (granule), the high blood sugar level of mice lowered to normal level. The results show that "Denhichi-Tochu-Sei" (granule) possesses the ability effectively to control the blood sugar level of mice suffering from diabetes.

TABLE 6

Effect of "Denhichi-Tochu-Sei" (granule) for mice on high blood sugar level

| Group | Number of animals | Dosage (g/kg) | Blood sugar level before the administration of "Denhichi-Tochu-Sei" (granule) (mg/dl) | Blood sugar level after the administration of "Denhichi-Tochu-Sei" (granule) (mg/dl) |
|---|---|---|---|---|
| Normal group (control) | 20 | | 12.11 ± 9.65 | |
| Group with high blood sugar level | 20 | | 340.15 ± 52.42 | |
| Group with high blood sugar level and a dosage of "Denhichi-Tochu-Sei" (granule) | 20 | 2 | 339.41 ± 50.21 | 290.47 ± 127.8 |

*$P < 0.05$ compared with group with high blood sugar level

EXAMPLE 6
Effect of "Denhichi-Tochu-Sei", "Gallae rhois" and "Licorice Root" (mixed extracts) for the Blood Cholesterol of Rats Suffering with Hyperlipemia:

Rats and mice were divided into following four groups (10 rats and mice for each group). They were A) normal group, B) a group suffering from hyperlipemia (with dosage of high fat feed), C) a group suffering from hyperlipemia (with high dosage of "Denhichi-Tochu-Sei", "Gallae rhois" and "Licorice Root" (hereinafter also referred to as mixed extracts), D) a group suffering from hyperlipemia (with a small amount of dosage of "Denhichi-Tochu-Sei", "Gallae rhois" and "Licorice Root" mixed extracts).

The composition of the mixed extracts in this example and the following examples was "Denhichi-Tochu-Sei" 20 weight %, "Gallae rhois" 8 weight % and "Licorice Root" 8 weight %. The C and D groups were given the mixed extracts and high fat feed in the stomach through cannula constantly for 30 days. One hour after the last administration, a blood sample was taken from rat ophthalmic vein, from which serum was separated. The serum was examined for the levels of cholesterol, triglyceride, lipoprotein of low molecular weight, LDL and lipoprotein of high molecular weight using Beckmann's serum biochemical analyzer CX5. The results are shown in Table 7.

It can be shown from the results of Table 7 that hyperlipemia was prevented when "Denhichi-Tochu-Sei", "Gallae rhois" and "Licorice Root" mixed extracts were added to high fat feed. Namely, the reduction of blood serum cholesterol, the reduction of lipoprotein with low molecular weight, the slight elevation of lipoprotein with higher molecular weight and reduction of triglyceride was observed in group C) and group D). Statistical and significant differences were obtained between the measurement value of normal group A) or group B) with only high fat feed and the values of 10 groups C) and D) with the mixed extracts.

production, NADPH oxidation and oxygen consumption.

TABLE 9

Effect for lipid peroxidation induced by carbon tetrachloride, lipid-binding for $^{14}CCl_4$, CO production, NADPH oxidation and oxygen consumption

| Mixture added | MDA production | Lipid-binding for $^{14}CCl_4$ | CO production | NADPH oxidation | Oxygen consumption |
|---|---|---|---|---|---|
| 0 | 100 | 100 | 100 | 100 | 100 |
| 100 mg | 78 | 89 | 92 | 72 | 60 |

Inhibitory effect
MDA: Malondialdehyde

TABLE 7

The effect of "Denhichi-Tochu-Sei" "Gallae rhois" and "Licorice Root" (mixed extracts, granule) on blood serum lipid levels

| Group | Number of animals | Dosage (g/kg) | Cholesterol (mol/l) | Lipoprotein of high molecular weight (mol) | LDL (mol/l) | Triglyceride (mol/l) | Lipoprotein of low molecular weight (mol/l) |
|---|---|---|---|---|---|---|---|
| Normal group | 10 | | 1.51 ± 0.3* | 1.05 ± 0.15* | 0.182 ± 0.15* | 0.911 ± 0.42* | 0.51 ± 0.18* |
| Group with a dosage of high fat feed | 10 | | 15.40 ± 3.0 | 0.54 ± 0.01 | 16.07 ± 1.03 | 2.551 ± 0.90 | 1.10 ± 0.40 |
| Group with high fat feed and high dosage of mixed extracts | 10 | 2 | 8.90 ± 2.0* | 0.50 ± 0.17* | 7.58 ± 3.13* | 1.89 ± 0.59* | 0.87 ± 0.30* |
| Group with high fat feed and low dosage of mixed extracts | 10 | 1 | 10.75 ± 1.9* | 0.50 ± 0.15* | 9.40 ± 3.40* | 2.30 ± 0.88* | 0.99 ± 0.21* |

*P < 0.05 Compared with group with a dosage of high fat feed

EXAMPLE 7
Effect for Hepatic Diseases of "Denhichi-Tochu-Sei", "Gallae rhois" and "Licorice Root" Mixed Extracts:

Table 8 shows the effect of "Denhichi-Tochu-Sei", "Gallae rhois" and "Licorice Root" mixed extracts for rats with hepatic disease (n=8) induced by D-glucosamine (800 mg/kg).

TABLE 8

Effect of "Denhichi-Todhu-Sei", "Gallae rhois" and "Licorice Root" mixed extracts (2000 mg/kg) for rats with hepatic disease (n = 8) induced by D-glucosamine (800 mg/kg)

|  | Normal group | Group with a dosage of mixed extracts |
|---|---|---|
| GPT ($\mu$ % ± S. D) | 1012 ± 220 | 730 ± 17 |
| GOT ($\mu$ % ± S. D) | 1696 ± 130 | 1252 ± 35 |

EXAMPLE 8
Effect of "Denhichi-Tochu-Sei", "Gallae rhois" and "Licorice Root" Mixed Extracts for Lipid Peroxidation Induced by Carbon Tetrachloride, Lipid-binding for $^{14}CCl_4$, CO production, NADPH Oxidation and Oxygen Consumption:

Table 9 shows the effect on lipid peroxidation induced by carbon tetrachloride, lipid-binding for $^{14}CCl_4$, CO

EXAMPLE 9

Effect for Mice with High Blood Sugar Level:

When streptozotocin solution (90 mg/kg) was administered i.v. daily to mice (body weight 21~23 g), the mice became conditioned with high blood sugar, reduced body weight and produced conditions with increasing drinking and urine.

This example used mice with blood sugar level of 180 mg/dl or more. The mice (weight 21~23 g) were divided into three groups, normal mouse group, mouse group with high blood sugar level and mouse group with high blood sugar level, and administered mixed extracts (granule). They were examined for their blood sugar levels. The results are shown in Table 10. After the mice with high blood sugar level received mixed extracts (granule), the high blood sugar level became close to normal level. The mixed extracts of the present invention (granule) can effectively control the elevation of the blood sugar level of mice suffering from diabetes.

TABLE 10

Effect of "Denhichi-Tochu-Sei", "Gallae rhois" and "Licorice Root" mixed extracts for mice on high blood sugar level

| Group | Number of animals | Dosage (g/kg) | Blood sugar level before the administration of the mixed extracts (granule) (mg/dl) | Blood sugar level after the administration of the mixed extracts (granule) (mg/dl) |
|---|---|---|---|---|
| Normal group (control) | 20 | | 112.20 ± 9.50 | |
| Group with high blood sugar level | 20 | | 330.15 ± 47.20 | |
| Group with high blood sugar level and a dosage of mixed extracts (granule) | 20 | 2 | 338.40 ± 50.20 | 285.40 ± 71.20 |

*$P < 0.05$ compared with group with high blood sugar level

From the above-mentioned experiments with animals, the following results are shown clearly.

1) The administration of "Denhichi-Tochu-Sei" and "Denhichi-Tochu-Sei", gallic acid-containing herbal extracts and "Licorice Root" mixed extracts show the lowering effect of hyperlipemia in rats and also the reduction of both serum cholesterol and lipoprotein of low molecular weight, the slight elevation of lipoprotein of high molecular weight and reduction of triglyceride in the mice.

2) The administration of "Denhichi-Tochu-Sei" results in activation of monocyte macrophage of mice with deteriorating immune system.

3) The long-term administration of "Denhichi-Tochu-Sei" is effective in enhancing the durability of mice against fatigue.

4) The administration of "Denhichi-Tochu-Sei", gallic acid-containing herbal extracts and "Licorice Root" mixed extracts are effective in the lowering of elevated serum GTP, GOT level in rats with hepatic disease induced by D-glucosamine.

5) The administration of "Denhichi-Tochu-Sei", gallic acid-containing herbal extracts and "Licorice Root" mixed extracts show the inhibitory effect in MDA production of rats induced by carbon tetrachloride, lipid-binding for $^{14}CCl_4$, CO production, NADPH oxidation and oxygen consumption.

6) The administration of "Denhichi-Tochu-Sei" and that of "Denhichi-Tochu-Sei", gallic acid-containing herbal extracts and "Licorice Root" mixed extracts have lowered blood sugar level of rats with high blood sugar induced by streptozotocin.

The above results show the preventive effects of "Denhichi-Tochu-Sei" for hyperlipemia and the significant reduction of blood sugar level by "Denhichi-Tochu-Sei" and also "Denhichi-Tochu-Sei", "Gallae rhois" and "Licorice Root" mixed extracts, or taking in food and feed with them added. And the mixed extracts play a role in improvement of hepatic function. These results prove that this invention can effectively improve the health of human beings and animals.

Moreover, it is noteworthy that no side effects including acute toxic side effect, were seen in any of the animal tests.

EXAMPLE 11

Treatment Effect of "Denhichi-Tochu-Sei", "Gallae rhois" and "Licorice Root" mixed Extracts for the Symptoms of Patients with Chronic Viral Hepatitis C A HCV patient (male, aged 50) was treated for about 3.5 months by interferons (IFN) and no improvements in his GOP and GTP were observed. On the other hand, after the patient was treated for ten days by the administration of "Denhichi-Tochu-Sei" "Gallae rhois" and "Licorice Root" mixed extracts, the GOP level was improved from 159 to 89 and the GTP from 204 to 48. The results are shown in Table 11.

TABLE 11

| | 93/9 | 94/1 The administration of IFN (Dec. To Mar.) | 95/4 | 95/5 | 95/7 | 96/3 | 96/9 | 99/1 The administration of mixed extracts DAY 1 | 99/2 DAY 10 |
|---|---|---|---|---|---|---|---|---|---|
| AST(GOT) | 187 | 82 | 145 | 119 | 134 | 155 | 119 | 159 | 89 |
| ALT(GTP) | 248 | 101 | | 109 | 178 | 205 | 189 | 204 | 48 |
| y-GTP | 252 | 167 | | | | | | 260 | 254 |

EXAMPLE 12

Treatment Effect of "Denhichi-Tochu-Sei", "Gallae rhois" and "Licorice Root" mixed Extracts for the Patients with Non-viral Hepatitis:

After a female patient with non-viral hepatitis was treated for ten days by the dosage of "Denhichi-Tochu-Sei", "Gallae rhois" and "Licorice Root" mixed extracts, the GOP level was reduced from 53 to 39 and the GTP from 58 to 35. The results are shown in Table 12.

TABLE 12

| | 94/2 | 94/7 | 94/10 | 95/1 | 95/6 | 95/12 | 96/2 | 96/3 | 96/7 | 97/3 | 97/10 | 98/4 | 98/12 The administration of mixed extracts (for 10 days) | 99/1 The second administration of mixed extracts (first day) | 8th day |
|---|---|---|---|---|---|---|---|---|---|---|---|---|---|---|---|
| AST(GOT) | 94 | 58 | 103 | 177 | 58 | 67 | 77 | 69 | 40 | 65 | 62 | 70 | 53 | 39 | 50 |
| ALT(GTP) | 127 | 73 | 454 | 160 | 79 | 59 | 106 | 96 | 47 | 97 | 72 | 97 | 58 | 35 | 17 |
| γ-GTP | 34 | | | | | | | | | | | | | | |

EXAMPLE 13
Effect of "Denhichi-Tochu-Sei", "Gallae rhois" and "Licorice Root" mixed Extracts for the Patient with Hepatitis B:

A patient (male, aged 70) with HBs antibody positive was treated for ten days with the dosage of "Denhichi-Tochu-Sei", "Gallae rhois" and "Licorice Root" mixed extracts. At the fourth day of the dosage, his GOP level was lowered from 28 to 23 and the GTP from 60 to 28. The results are shown in Table 13.

TABLE 13

| | 99/1 | | | |
|---|---|---|---|---|
| | Hospitalized | The administration of mixed extracts (first day) | (fourth day) | 99/2 (eighth day) |
| AST (GOT) | 55~115 | 82 | 23 | 27 |
| ALT (GTP) | 56~123 | 60 | 28 | 15 |
| γ-GTP | 33~51 | 35 | 27 | 24 |

EXAMPLE 14
Effect of "Denhichi-Tochu-Sei", "Gallae rhois" and "Licorice Root" mixed Extracts for Patients with Drug Hepatitis:

A patient (male, aged 30) with drug hepatitis was treated for ten days with the dosage of "Denhichi-Tochu-Sei", "Gallae rhois" and "Licorice Root" mixed extracts. At the fifth day after the stop of administration, the GOP level was lowered from 43 to 32 and the GTP from 121 to 27. The results are shown in Table 14.

TABLE 14

| | '98/11 Leaving hospital | '99/1 Beginning the administration of mixed extracts | The fifth day after the stop of administration | The 17th day after the stop of administration |
|---|---|---|---|---|
| AST (GOT) | 66 | 43 | 32 | 38 |
| ALT (GTP) | 200 | 121 | 27 | 88 |

EXAMPLE 15
Effect of "Denhichi-Tochu-Sei", "Gallae rhois" and "Licorice Root" mixed Extracts for the Symptoms of Patients with Chronic Active Hepatitis C:

A patient with abnormal liver function (GOT 80, GTP 102, y-GTP 68) received a dosage of interferons three times a week for two weeks. At the eleventh day of the dosage, side effects appeared. Thereafter, instead of interferons, the "Denhichi-Tochu-Sei" was given in a dose of 6 g per day for six days. The side effects disappeared and the liver function became better (GOT 60, GTP 47, y-GTP 17). However, the amount of viruses still remained unchanged. After leaving the hospital, the patient received interferons three times a week and about two weeks later, "Denhichi-Tochu-Sei", "Gallae rhois" and "Licorice Root" mixed extracts in a dose of 3 g per day for a week. The amount of viruses was reduced to 0.5 Meq/ml or less. The liver function returned to the normal condition (GOT 31, GPT8, y-GTP 14). The normal liver function (GOT 25, GTP 9, y-GTP 12) was obtained after two months of the administration of "Denhichi-Tochu-Sei", "Gallae rhois" and "Licorice Root" mixed extracts. The results are shown in Table 15.

TABLE 15

| | 7/29 | 8/18 | 8/19 *1 | 8/25 | 9/11 *2 | 9/18 | 11/24 |
|---|---|---|---|---|---|---|---|
| AST (GOT | 80 | 50 | | 60 | | 31 | 25 |
| ALT (GTP) | 102 | 58 | | 47 | | 8 | 9 |
| γ-GTP | 68 | 83 | | 17 | | 14 | 12 |

*1 The administration of interferons and "Denhichi-Tochu-Sei" were started
*2 "Denhichi-Tochu-Sei", "Gallae rhois" and "Licorice Root" mixed extracts As explained above, "Denhichi-Tochu-Sei" and "Denhichi-Tochu-Sei", gallic acid-containing herbal extracts and "Licorice Root" mixed extracts of this invention can be used as food supplement (feed supplement) for healthcare. The compositions of this invention are proved to be effective in protection against hypertension and liver disorders. They also proved to be useful for healthcare and improvement of nutritional state and immune system. Especially, in the case of the mixed preparation of gallic acid-containing herbal extracts and "Licorice Root" with "Denhichi-Tochu-Sei", both components can be easily absorbed into the body of human beings and animals. In addition, the rapid effects with the above-mentioned preparation are observed.

What is claimed is:

1. A composition comprising from 10–70% weight % of a water extract of *Panax pseudo-ginseng* and from 10–70% weight % of a water extract of *Eucommia ulmoides* further comprising a water extract of a gallic acid containing herbal extracts and a water extract of Licorice root.

2. A medicine comprising the composition of claim 1.

3. A food supplement comprising the composition of claim 1.

4. The food supplement of claim 3 comprising from 20–76 weight % of a combination of water extracts of *Panax pseudo-ginseng* and *Eucommia ulmoides*; and from 4–20 weight % of water extracts of gallic acid containing herbs; and from 4–15 weight % of water extracts of Licorice root.

5. A healthcare food comprising 0.1~20 weight % of the food supplement of claim 3.

6. The healthcare food of claim 5 in the form of powder, powder granule, tablet, drink or emulsion.

7. A mixed feed comprising the composition of claim 1.

8. A feed comprising the mixed feed of claim 7.

9. A method for producing the composition of claim 1 comprising:
    obtaining condensed extracts of *Panax pseudo-ginseng* by heat drying hot water extracts of minced dry *Panax pseudo-ginseng*;
    obtaining condensed extracts of *Eucommia ulmoides* by heat drying hot water extracts of minced dry *Eucommia ulmoides*;
    obtaining condensed extracts of gallic acid-containing herbs by heat drying hot water extracts of minced dry gallic acid-containing herbs;
    obtaining extracts of Licorice root;
    mixing the condensed extracts of *Panax pseudo-ginseng*, *Eucommia ulmoides*, gallic acid-containing herbs and extracts of Licorice root; and
    drying the mixture.

10. The method of claim 9 wherein the extracts of *Panax pseudo-ginseng* contain pulverized *Panax pseudo-ginseng*.

11. The method of claim 9 wherein the extracts of *Eucommia ulmoides* contain pulverized *Eucommia ulmoides*.

12. A composition comprising from 30–90 weight % of a water extract of *Panax-Pseudo-Ginseng* and from 10–70 weight % of a water extract of *Eucommia ulmoides*.

13. A composition comprising from 10–60 weight % of a water extract of *Panax-Pseudo-Ginseng* and from 40–90 weight % of a water extract of *Eucommia ulmoides*.

14. The composition of claim 12 whereby the water extract of *Eucommia ulmoides* is 40 weight %.

15. The composition of claim 12 whereby the water extract of *Panax-Pseudo-Ginseng* is 30 weight %.

16. The composition of claim 12 whereby the water extract of *Panax-Pseudo-Ginseng* is 30 weight % and the water extract of *Eucommia ulmoides* is 40 weight %.

17. The composition of claim 13 whereby the water extract of *Panax-Pseudo-Ginseng* is 30 weight %.

18. The composition of claim 13 whereby the water extract of *Eucommia ulmoides* is 40 weight %.

19. A method for producing the composition of claim 12 or 13 comprising:
    obtaining condensed extracts of *Panax pseudo-ginseng* by heat drying hot water extracts of minced dry *Panax pseudo-ginseng*; and
    obtaining condensed extracts of *Eucommia ulmoides* by heat drying hot water extracts of minced dry *Eucommia ulmoides*;
    mixing the condensed extracts of *Panax pseudo-ginseng* and *Eucommia ulmoides*; and
    drying the mixture.

20. The method of claim 19 wherein the extracts of *Panax pseudo-ginseng* contain pulverized *Panax pseudo-ginseng*.

21. The method of claim 19 wherein the extracts of *Eucommia ulmoides* contain pulverized *Eucommia ulmoides*.

22. The method of claim 9 wherein the extracts of gallic acid-containing herbs contain pulverized gallic acid-containing herbs.

23. The method of claim 9 wherein the extracts of Licorice root contain pulverized Licorice root.

* * * * *